United States Patent [19]
Abell et al.

[11] Patent Number: 5,756,479
[45] Date of Patent: May 26, 1998

[54] FLAVIN ADENINE DINUCLEOTIDE ANALOGUE INHIBITORS OF MONOAMINE OXIDASE

[75] Inventors: Creed W. Abell; Sau-Wah Kwan; Binhua Zhou; Blain M. Mamiya; Duane A. Lewis, all of Austin, Tex.

[73] Assignee: Research Development Foundation, Carson City, Nev.

[21] Appl. No.: 449,311

[22] Filed: May 24, 1995

Related U.S. Application Data

[63] Continuation-in-part of Ser. No. 365,782, Dec. 29, 1994, abandoned.

[51] Int. Cl.$^6$ .................... A61K 31/70; C07H 19/207
[52] U.S. Cl. .................................... 514/47; 536/26.25
[58] Field of Search .................... 536/26.25, 27.14; 514/47

[56] References Cited

FOREIGN PATENT DOCUMENTS 9511028  4/1995  WIPO.

OTHER PUBLICATIONS

Pinto et al., "Inhibition of Riboflavin Metabolism in Rat Tissues by Chloropromazine, Imipramine, and Amitriptyline," *J. Clin. Invest.*, 67(4),1500–1506 (1981).
Weyler et al., "Catalytically Active Monoamine Oxidase Type A from Human Liver Expressed in *Saccharomyces cerevisiae* Contains Covalent FAD," *Biochem. Biophys. Res. Comm.*, 173(3), 1205–1211 (1990).
Gomez et al., "A Comparative Study of Some Kinetic and Molecular Properties of Microsomal and Mitochondrial Monoamine Oxidase," *Biochemical Pharmacology*, 37(18), 3407–3413 (1988).
Barber et al., "Anti–Flavin Antibodies," *Biochemical Journal*, 242, 89–95 (1987).
T. W. Stone (I), "Adenine Dinucleotide Effects in the Nervous System," in *Physiology and Pharmacology of Adenosine Derivatives*, Daly et al. eds., Raven Press, New York, NY, 1983, pp. 237–244.
Tat'yanenko et al., "Tyramine Oxidase Studied Using Structural Analogs of Flavine Adenine Dinucleotide, *Mol. Biol. (Moscow)*, 8(6), 871–878 (1974); *Chem. Abstr.*, 82(17), p.185, Abstr. No. 108082k (1975); only Abstract supplied.
McCormick et al., "Coenzyme Specificity of D–Amino Acid Oxidase for the Adenylate Moiety of FAD," *Biochim. Biophys. Acta*, 89, 4476–452 (1964).
Wierenga et al., "Prediction of the Occurrence of the ADP–binding βαβ–fold in Protiens, Using an Amino Acid Sequence Fingerprint," *J. Mol. Biol.*, 187, 101–107 (1986).
Abell et al., "Molecular and Functional Properties of the Monoamine Oxidases," *Heterocycles*, 39(2), 933–955 (1994).
T. W. Stone (II), "Actions of Adenine Dinucleotides on the Vas Deferens, Guinea–Pig Taenia Caeci and Bladder," *European J. of Pharmacology*, 75(2–3), 93–102 (1981).

*Primary Examiner*—John Kight
*Assistant Examiner*—L. Eric Crane
*Attorney, Agent, or Firm*—Benjamin Aaron Adler

[57] ABSTRACT

The present invention provides an inhibitor of monoamine oxidase comprising a modified synthetic flavin adenine dinucleotide compound. Also provided is a method of inhibiting monoamine oxidase enzymatic activity in a cell, comprising the step of contacting said cell with a pharmacologically effective dose of a modified synthetic flavin adenine dinucleotide compound. Further provided is a method of treating a brain pathophysiological state in an individual, comprising administering a therapeutically effective dose of a modified synthetic flavin adenine dinucleotide compound to said individual.

3 Claims, 8 Drawing Sheets

Figure 1

| cDNA Clones | Mutation Primer | Side Chain | |
|---|---|---|---|
| WT | 34<br>N  V  V  V  L  E  A  R  D  R  V<br>AATGTGGTTGTTCTGGAAGCCCGGGACCGTGTG | -CH$_2$-CH$_2$-COO$^-$ | SEQ ID No. 10<br>SEQ ID No. 3 |
| E34D | D<br>AATGTGGTTGTTCTGGAcGCCCGGGACCGTGTG | -CH$_2$COO$^-$ | SEQ ID No. 4 |
| E34Q | Q<br>AATGTGGTTGTTCTGcAGGCCCGGGACCGTGTG | -CH$_2$-CH$_2$-CONH$_2$ | SEQ ID No. 5 |
| E34A | A<br>AATGTGGTTGTTCTGGcgGCCCGGGACCGTGTG | -CH$_3$ | SEQ ID No. 6 |
| WT | 10<br>D  V  V  V  V  G  G  G  I<br>CGACGTGGTCGTGGTGGGGGGCGGCATC | -CH(CH$_3$)-CH$_3$ | SEQ ID No. 11<br>SEQ ID No. 7 |
| V10I | I<br>CGACGTGGTCGTGaTcGGGGGCGGCATC | -CH(CH$_3$)-CH$_2$-CH$_3$ | SEQ ID No. 8 |

Figure 1

| cDNA Clones | Mutagenic Primers | Amino Acid Side Chain | |
|---|---|---|---|
| WT | CGTGTGGGAGGCAGGACTTACACTCTTAGGAACC<br>　　　　　　　　　　　　　　$\underline{44}$<br>　　　　　　　　　　　　　　Y | -CH$_2$-◯-OH | SEQ ID No. 12 |
| Y44F | CGTGTGGGAGGCAGAACgTtCACTCTTAGGAACC<br>　　　　　　　　　　　　$\underline{\text{Psp1406I}}$<br>　　　　　　　　　　　　F | -CH$_2$-◯ | SEQ ID No. 13 |
| Y44S | GGGAGGCAGGACgTcCACTCTTAGGAAC<br>　　　　　　　$\underline{\text{AatII}}$<br>　　　　　　　S | -CH$_2$-OH | SEQ ID No. 14 |
| Y44A | GGGAGGCAGGACggcCACTCTTAGGAACC<br>　　　　　　　$\underline{\text{EaeI}}$<br>　　　　　　　A | -CH$_3$ | SEQ ID No. 15 |
| WT | GGCAGGACTTACACTCTTAGGAACCAAAAGGTTAAATATGTGG<br>　　　　　　　　　$\underline{46}$<br>　　　　　　　　　L | -CH$_2$-CH(CH$_3$)$_2$ | SEQ ID No. 16 |
| L46V | GGCAGGACTTACACTgTTcGaAACCAAAAGGTTAAATATGTGG<br>　　　　　　　　　　$\underline{\text{BstBI}}$<br>　　　　　　　　　V | -CH(CH$_3$)$_2$ | SEQ ID No. 17 |

Figure 5

FLAVIN ADENINE DINUCLEOTIDE ANALOGUE INHIBITORS OF MONOAMINE OXIDASE

CROSS-REFERENCE TO RELATED APPLICATION

This application is a continuation in part of U.S. patent application Ser. No. 08/365,782, filed Dec. 29, 1994, now abandoned.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the fields of neuropharmacology and protein chemistry. More specifically, the present invention relates to novel flavin adenine dinucleotide analogues as inhibitors of monoamine oxidase.

2. Description of the Related Art

Neurons in the brain communicate through the release and uptake of chemicals called neurotransmitters. The concentration of neurotransmitters is controlled in part by enzymes that produce and metabolize the neurotransmitters. Two such enzymes, monoamine oxidase A and B [MAO A and B; amine: oxygen, oxidoreductase (deaminating, flavin-containing), EC 1.4.3.4] are the major intracellular enzymes in the central nervous system and peripheral tissues of mammals that catalyze the oxidative deamination of neuroactive and vasoactive amines. These enzymes are integral proteins of the outer mitochondrial membrane and can be distinguished by differences in substrate preference, inhibitory specificity, tissue and cell distribution, and immunological properties. Furthermore, the nucleotide and deduced amino acid sequences definitively show that monoamine oxidase A and B are two distinct proteins. Comparative studies between the human and rat sequences show that the monoamine oxidase A and B proteins have approximately 70% identity and the respective A and B enzymes have very high sequence identity in both species, particularly in the two regions of the molecule that bind flavin adenine dinucleotide (FAD) covalently and non-covalently.

Monoamine oxidases A and B have been linked to various psychiatric and neurological disorders and each is a target for certain psychiatric and neurologic drugs. For example, the monoamine oxidase A inhibitor moclobemide and the monoamine oxidase B inhibitor deprenyl have been used for the treatment of unipolar depression and Parkinson's disease, respectively. Thus far, none of the available drugs is totally satisfactory. In fact, some of these drugs, such as parnate, do not distinguish between monoamine oxidase A and B, and some monoamine oxidase inhibitors produce life threatening side-effects such as hypertensive crisis.

Current interest in monoamine oxidase A has been intensified by the discovery of an alteration in its gene. Defective monoamine oxidase A, due to a mutation of CAG (glutamine) to TAG (termination codon), was identified in some members of a Dutch family who exhibit abnormal aggressive behavior. A role for monoamine oxidase B in idiopathic Parkinson's disease has received support through the identification of 1-methyl-4-phenyl-1, 2, 3, 6,-tetrahydropyridine (MPTP), a powerful neurotoxin. This substance was found as a contaminant in a synthetic heroin and produced a Parkinsonian syndrome in some individuals who self-administered the synthetic heroin. MPTP is oxidized by monoamine oxidase B to a reactive species (MPP$^+$). Pretreatment of primates with deprenyl (a monoamine oxidase B selective inhibitor), but not clorgyline (a monoamine oxidase A selective inhibitor), prevents the development of MPTP-induced parkinsonism. Treatment of hundreds of Parkinson's patients with deprenyl showed that this drug significantly slowed the rate of deterioration and the course of the disease. Also, an alternate allele of the monoamine oxidase B gene has been identified in patients with Parkinson's disease, a finding which suggests that an inherited variant form of monoamine oxidase B may be associated with a genetic predisposition for this neurological disorder. Novel monoamine oxidase inhibitors that are designed to interact with functionally important regions of the enzymes may have high efficacy for treatment of depression and Parkinson's disease with minimal side effects.

In order to design new drugs having greater selectivity and efficacy for these diseases, it is important to determine the structure of the functional regions of monoamine oxidase A and B, including the active site. Monoamine oxidase A and B are large proteins that have subunit molecular weights of approximately 60,000. Neurotransmitters and drugs that bind to these enzymes have small molecular weights in the range of hundreds, not thousands. Consequently, the drugs interact with only a small segment of the enzyme, such as the active site or the site to which an essential cofactor binds. Monoamine oxidase A and B use the cofactor, flavin adenine dinucleotide (FAD). FAD binds to two different sites on both enzymes, one covalently and the other non-covalently, and these interactions are essential steps for monoamine oxidase A and B to function.

Knowledge of the secondary and tertiary structure of monoamine oxidase A and B would be of great value for the design of new drugs that have high efficacy for these diseases with minimal side effects. Since the monoamine oxidases are integral proteins of the outer mitochondrial membrane, however, it has been difficult to obtain crystals suitable for X-ray diffraction studies. Alternatively, a search for sequence similarities between monoamine oxidase A and B and other proteins of known structure may be useful for identifying common structural motifs.

The prior art is deficient in the lack of effective means of inhibiting the enzymatic activity of monoamine oxidase A and B for the endpoint of therapeutically treating various psychiatric and neurological disorders without side effects. The present invention fulfills this longstanding need and desire in the art.

SUMMARY OF THE INVENTION

In one embodiment of the present invention, there is provided an inhibitor of monoamine oxidase comprising a modified synthetic flavin adenine dinucleotide compound.

In another embodiment of the present invention, there is provided a pharmaceutical composition of the present invention and a pharmaceutically acceptable carrier.

In yet another embodiment of the present invention, there is provided a method of inhibiting monoamine oxidase enzymatic activity in a cell, comprising the step of contacting said cell with a pharmacologically effective dose of a modified synthetic flavin adenine dinucleotide compound.

In still yet another embodiment of the present invention, there is provided a method of treating a brain pathophysiological state in an individual, comprising administering a therapeutically effective dose of a modified biosynthetic flavin adenine dinucleotide compound to said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the human monoamine oxidase B mutants. Oligonucleotide primers of wild-type and mutants, and side chains corresponding to their amino acid substitutions are shown. Lower case letters indicate base substitutions. Bold letters indicate amino acid substitutions for the glutamate residue in position 34 in mutants E34A, E34Q and E34D, and valine in position 10 in mutant V10I.

FIG. 5 shows nucleotide sequences of mutagenic primers in site-directed mutagenesis studies. Lowercase letters indicate base substitutions. The codon for wild-type and mutants at positions 44 and 46 are indicated by a single line above the nucleotides. Base substitutions which do not alter the amino acid coding sequence were also included in each mutagenic primer to create a new restriction site (double underline) for the purpose of screening. Side chains corresponding to amino acid substitutions are also shown.

DETAILED DESCRIPTION OF THE INVENTION

Figure 2:
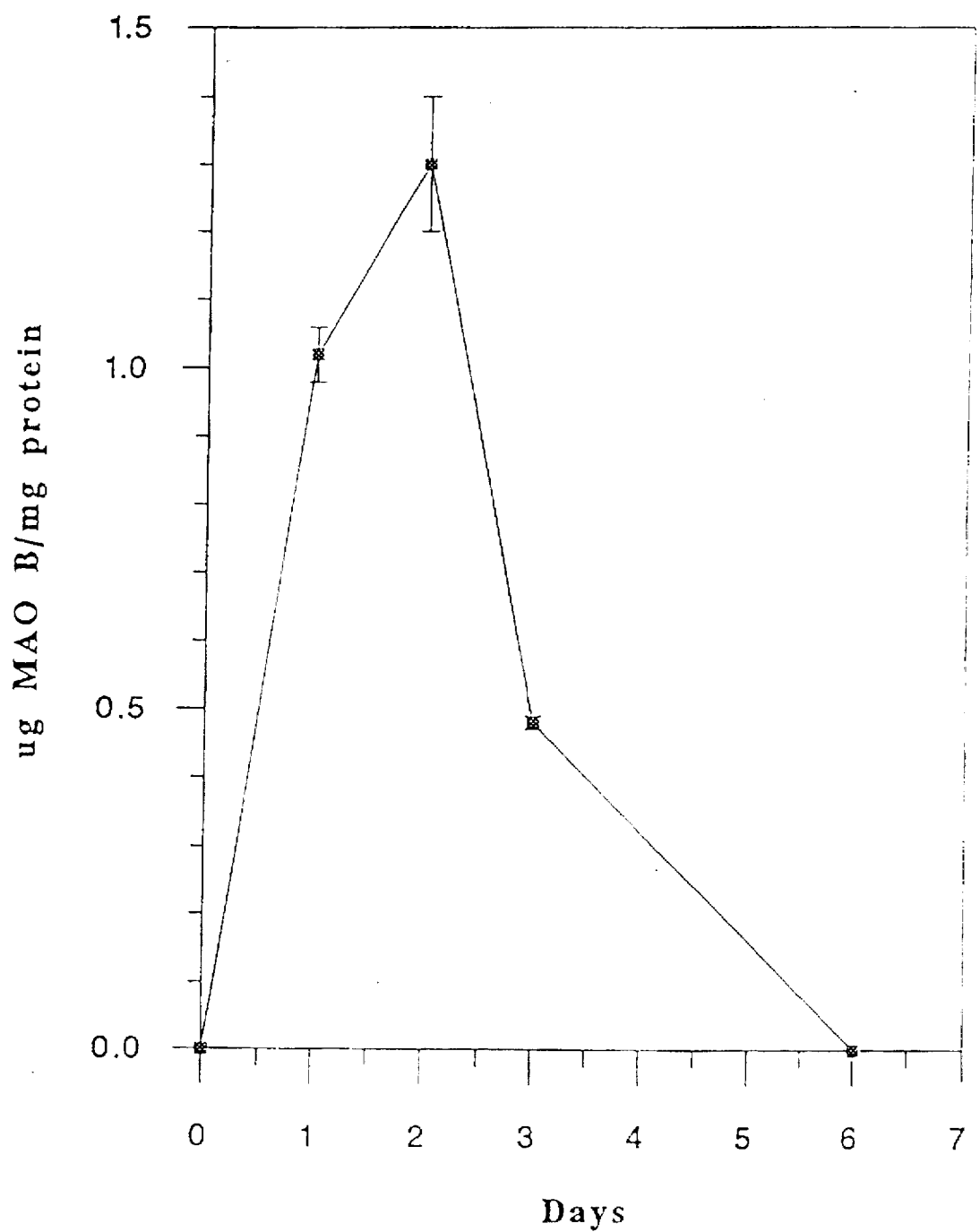
FIG. 2 shows the monoamine oxidase B expression in COS-7 cells. Transient expression of monoamine oxidase B in mammalian COS-7 cells was obtained by electroporation as described below. The expression was quantitated by ELISA on consecutive days to determine the incubation time required to obtain the maximum expression level. The maximal expression was found to be at day 2, resulting in a concentration of 1.3 µg of monoamine oxidase B/mg of total protein (mean±S.E., n=3) in cell lysates.

The present invention illustrates the structural requirements for binding of FAD to monoamine oxidase B. Replacing glutamate in position 34 with aspartate, glutamine or alanine and replacing valine in position 10 with isoleucine by site-directed mutagenesis had dramatic and unexpected effects. The effect of these amino acid substitutions on monoamine oxidase B activity was demonstrated in COS-7 cells transfected with wild-type and mutant cDNAs encoding the normal and variant enzymes. As is shown by the present invention, Glu$^{34}$ plays a critical role in the catalytic integrity of monoamine oxidase B and provides increased insight into the structure and function of this $\beta_1$-$\alpha$-$\beta_2$ motif.

The cDNA clones for monoamine oxidase A and B have been isolated and the nucleotide and deduced amino acid sequences determined. Monoamine oxidase A and B consist of 527 and 520 amino acid residues with calculated subunit molecular weights of 59,700 and 58,800, respectively. These enzymes have a high sequence identity (approximately 70%) but those residues that differ occur at the same place throughout the polypeptide chains, indicating that monoamine oxidase A and B are derived from separate genes rather than by a splicing mechanism. The genes for human monoamine oxidase A and B consist of 15 exons and 14 introns with identical exon-intron organization.

Monoamine oxidase A and B contain at least four functional regions, including a FAD-binding site at the amino terminal end that is found in the vast majority of flavin-requiring enzymes. The other functional regions include a region of unknown function near the middle of the molecule, the FAD-covalent binding site toward the C-terminal end and the 28 amino acid residues on the carboxyl terminal end of the protein that anchors the enzymes to the outer mitochondrial membrane.

The present invention is directed to a composition of matter that is an inhibitor of monoamine oxidase comprising a modified synthetic flavin adenine dinucleotide compound. The inhibitor of the present invention is effective against both monoamine oxidase A and monoamine oxidase B.

Generally the flavin adenine dinucleotide compound disclosed by the instant application is one which interacts with glutamate-34 of monoamine oxidase to disrupt its enzymatic efficacy. Preferably, the flavin adenine dinucleotide compound is modified by removing a hydroxyl group from its adenosine monophosphate moiety. Preferably the hydroxyl group removed is either the 2' hydroxyl group and/or the 3' hydroxyl group. Most preferably, the inhibitor is selected from the group consisting of flavin deoxyadenosine dinucleotide and flavin dideoxyadenosine dinucleotide.

The present invention also provides a method of inhibiting monoamine oxidase enzymatic activity in a cell, comprising the step of contacting said cell with a pharmacologically effective dose of a modified synthetic flavin adenine dinucleotide compound. The method of inhibiting monoamine oxidase enzymatic activity is effective against both monoamine oxidase A and B.

The present invention also provides a method of treating a brain pathophysiological state in an individual, comprising administering a therapeutically effective dose of a modified synthetic flavin adenine dinucleotide compound to said individual. Representative examples of brain pathophysiological states include depression, Parkinson's disease, phobic-anxiety states, bulemia, post-traumatic reactions, obsessive-compulsive disorders and narcolepsy.

It is specifically contemplated that pharmaceutical compositions may be prepared using the novel modified biosynthetic flavin adenine dinucleotide compound of the present invention. In such a case, the pharmaceutical composition comprises the novel modified synthetic flavin adenine dinucleotide compound of the present invention and a pharmaceutically acceptable carrier. A person having ordinary skill in this art would readily be able to determine, without undue experimentation, the appropriate dosages and routes of administration of the novel modified synthetic flavin adenine dinucleotide compound of the present invention. Generally, the pharmaceutical composition of the present invention is administered in a dose of from about 0.1 mg/kg to about 20 mg/kg.

The following examples are given for the purpose of illustrating various embodiments of the invention and are not meant to limit the present invention in any fashion.

EXAMPLE 1

Site-directed Mutagenesis

Mutagenesis was carried out with a "Transformer Site-directed Mutagenesis" kit (Clontech) according to the manufacturer's protocol. In this method, a second oligonucleotide (Selection Primer) is used in addition to the mutagenic oligonucleotide (Mutagenic Primer) to introduce a restriction site mutation unique to the plasmid for the purpose of selection. The human monoamine oxidase B cDNA (Bach et al., 1988, Proc. Natl. Acad. Sci., 85:4934–4938) was cloned into the EcoRI site of the pBluescript SK vector (Stratagene). A HpaI restriction site was introduced into the 30-mer "Selection Primer" to replace the KpnI site in the plasmid vector (5'-CGAGGGGGGGGCCCGGGTACCCAATTCGCCC-3' to 5'-CGAGGGGGGGGCCCGGtTAaCCAATTCGCCC-3'). All oligonucleotides were custom synthesized by National Biosciences (FIG. 1). The glutamate residue in position 34 was replaced with alanine in E34A, glutamine in E34Q, aspartate in E34D, and the valine residue in position 10 was replaced with isoleucine in V10I (FIG. 1). Simultaneous annealing of the two primers was performed, followed by elongation and ligation. The reaction mixture containing the mutant and wild-type plasmids was transformed into mutS E. coli which is defective in mismatch repair. All transformants were grown up as a pool. The DNA was isolated and subjected to selective restriction with KpnI, which linearized the parental plasmid. A final transformation using the thoroughly restriction digested DNA resulted in isolation of the desired mutant. Each mutant was further characterized by sequencing using the dideoxy chain termination method (Sanger et al., 1977, Proc. Natl. Acad. Sci. 74: 5463–5467). The mutant cDNAs were then subdloned into the pSVK3 expression vector (LKB-Pharmacia) at the EcoRI site and screened for clones with the mutant insert in the sense orientation. This expression vector contains the colE1 origin for efficient replication in E. coli, an SV40 origin and the SV40 early promoter. Both the wild-type and mutant plasmid DNAs were purified through CsCl-gradients for transfection studies.

EXAMPLE 2

Transfection and Transient Expression

Wild-type and mutant monoamine oxidase B cDNAs were transiently transfected into COS-7 cells by electroporation using a method described by Zimmerman et al., J. Membr. Biol., 67:165–182 (1982). Cells were harvested during late log phase growth and resuspended to a concentration of $3.125 \times 10^6$ cells/ml in DMEM supplemented with 10% fetal bovine serum (FBS). Fifteen micrograms of normal or mutant cDNA were added to 0.8 ml ($2.5 \times 10^6$ cells) of cell suspension. Electroporation was carried out in a Bio-Rad Gene Pulser with a setting of 0.25 kV and 500 uF. Cells were resuspended in 15 ml of DMEM/FBS and incubated at 37° C. with 5% $CO_2$ for 48 hours.

EXAMPLE 3

Monoamine oxidase extraction

Transfected COS-7 cells were harvested at 48 hours and homogenized in a lysis solution containing 20 mM Tris-HCl, 1.0 mM EDTA, and 0.5 mM phenylmethylsulfonyl fluoride (PMSF). Sucrose was added to a final concentration of 0.25M followed by centrifugation at 400 xg for 3 minutes. The pellets were resuspended in 20 mM Tris-HCl, 0.5 mM EDTA, 0.5 mM PMSF, 0.25M sucrose, pH 8.0, and centrifuged as above. The two supernatants were combined for each sample and centrifuged at 50,000 x g for 1 hour in a Beckman Airfuge. The pellets containing the mitochondrial fractions were resuspended in 200 µl of PBS and gently homogenized. Five microliters of pure 10% Triton X-100 (Pierce) was added to each sample, and the samples were allowed to stir for 30 minutes at room temperature.

EXAMPLE 4

Production of goat antibodies to monoamine oxidase B

Polyclonal antibodies to monoamine oxidase B were obtained from a goat immunized with purified bovine liver monoamine oxidase B. The goat (Sunset Farm, Acadia Tex.) was given a subcutaneous injection of 0.5 mg of the antigen in Freund's complete adjuvant (Difco) followed by two subsequent injections in Freund's incomplete adjuvant at one week intervals. Three weeks after immunization, approximately 300 ml of blood was collected at two week intervals. The blood was allowed to clot and serum subjected to a 50% ammonium sulphate precipitation, then dialyzed against PBS. The antibody was further purified by passage through a CM Affi-Gel blue column (Bio-Rad).

EXAMPLE 5

Enzyme Linked Immunosorbance Assay (ELISA)

Protein concentrations of samples containing wild-type or mutant monoamine oxidase B were determined by a Micro-BCA kit (Pierce). All samples were then adjusted to equal protein concentration prior to quantitation of monoamine oxidase B. Samples were assayed by a modification of the ELISA (Yeomanson and Billet, *Biochemica et Biophysica Acta* 1116: 261–268 (1992), using a goat polyclonal anti-monoamine oxidase B antibody. Purified beef liver monoamine oxidase B was used for microtiter plate coating and standards. Monoamine oxidase B used for standards was purified by the method of Weyler and Salach, *Arch Biochem. Biophys.* 212:147–153 (1981) and determined to be 99% pure by SDS-polyacrylamide gel electrophoresis. Quantitation of competing polyclonal anti-monoamine oxidase B antibody was obtained by saturation with rabbit anti-goat horseradish peroxidase-conjugated antibody (Sigma). Detection was carried out by adding 320 µM TMB (3, 3', 5, 5'-tetramethylbenzidine), 1.3 mM $H_2O_2$ in 0.1M citric acid buffer pH 6.0. The reaction was developed at room temperature for 10 minutes and terminated by addition of 3.6N $H_2SO_4$ 100 µl/well. The absorbance was then detected at 450 nm using a Biotec EL310 Microplate Autoreader.

EXAMPLE 6

Enzyme Activity Determination

Monoamine oxidase B activity was assayed radiometrically by a modification of Wurtman and Axelrod, *Biochem. Pharmacol.* 12:1439–1440 (1963). Briefly, equal amounts of wild-type or mutant monoamine oxidase B (based on ELISA) from mitochondrial subcellular fractions were incubated in the assay mixture containing 0.05M sodium phosphate buffer, pH 7.4, 3.6 µmole of 55 µCi/mmole [$^{14}$C] benzylamine hydrochloride (Amersham), and 10 µmoles of unlabeled benzylamine. Sample were run in triplicate, and one out of each set was denatured with 6N HCl prior to the addition of substrate to serve as an internal control. After a 9 minute incubation at 37° C., all reactions were terminated with 25 µl of 6N HCl. The reaction product was extracted with toluene, and an aliquot of the organic phase was counted in liquid scintillation fluid in a Beckman LB3801 model liquid scintillation counter.

EXAMPLE 7

Immunoprecipitation of wild-type and mutant monoamine oxidase B

Transfected COS-7 cells were homogenized in 300 µl of 20 mM Tris HCl, 150 mM NaCl, 1 mM EDTA, 0.5 mM PMSF, pH 8.0 and monoamine oxidase B was extracted with 0.25% Triton X-100 for 30 minutes at 4° C. After centrifugation at 1300 xg for 5 minutes, the supernatants were incubated overnight at 4° C. with 10 µg of polyclonal goat anti-monoamine oxidase B antibody. Protein-G Sepharose beads (Pierce) were added (50 µl) and incubation continued for 3 hours. The protein-G sepharose/goat antibody/ monoamine oxidase B immunocomplex was collected by centrifugation at 10,000 xg for 20 seconds, and washed 6 times with 20 mM Tris buffer, pH 8.0. Bound proteins were eluted with SDS-PAGE sample buffer and subsequently analysed.

EXAMPLE 8

Western Blot Analysis

The immunoprecipitated proteins (obtained as described above) were subjected to electrophoresis in a 10% SDS-polyacrylamide gel and electrotransferred to a nitrocellulose membrane (S&S). The membrane was first blocked with 5% nonfat dry milk, then incubated with mouse monoamine oxidase B-1C2 monoclonal antibody overnight. Secondary antibody (biotin-conjugated goat anti-mouse antibody) was added and the membrane further incubated for 3 hours with streptavidin and biotin-conjugated alkaline phosphatase complex (Bio-Rad). Following extensive washing, the blot was developed by addition of nitro-blue-tetrazolium/5-bromo-4-chloro-3-indoyl phosphate (Bio-Rad) as substrate.

EXAMPLE 9

Quantitation and expression of Wild-type and mutant monoamine oxidase B

The parameters of wild-type monoamine oxidase B expression under varying conditions were characterized. Optimal electroporation was achieved when $3.1 \times 10^6$ COS-7 cells/ml were transfected with 15 µg of cDNA, resulting in the synthesis of approximately 1.3 µg of monoamine oxidase B per mg of total cellular protein. The use of larger cell numbers did not increase the total amount of monoamine oxidase B obtained and decreased the amount of monoamine oxidase B obtained per cell. Although use of cDNA concentrations higher than 15 µg/0.8 ml did result in slightly higher expression levels, the increases were nonlinear, and doubling the cDNA concentration (30 µg/0.8 ml) resulted in less than a 10% increase in expressed monoamine oxidase B (data not shown). Culture times after electroporation were also examined, and the peak production of monoamine oxidase B using $2.5 \times 10^6$ cells was found to occur at 48 hours (FIG. 2). Furthermore, the voltage and capacitance parameters were optimal when V=250 and uF =500. To monitor the consistency of pulses used to produce transfection, the time required for each exponential pulse to decay to ~37% of the maximal voltage (time constant) was recorded for each sample as follows; Wild-type=13.4±0.4 mSec, E34A= 12.7±0.3 mSec, E34Q=13.1±0.2 mSec, E34D=13.2±0.1 mSec, and V10I=13.3±0.2 mSec (±is the standard error of the mean, where n>3).

Figure 4:
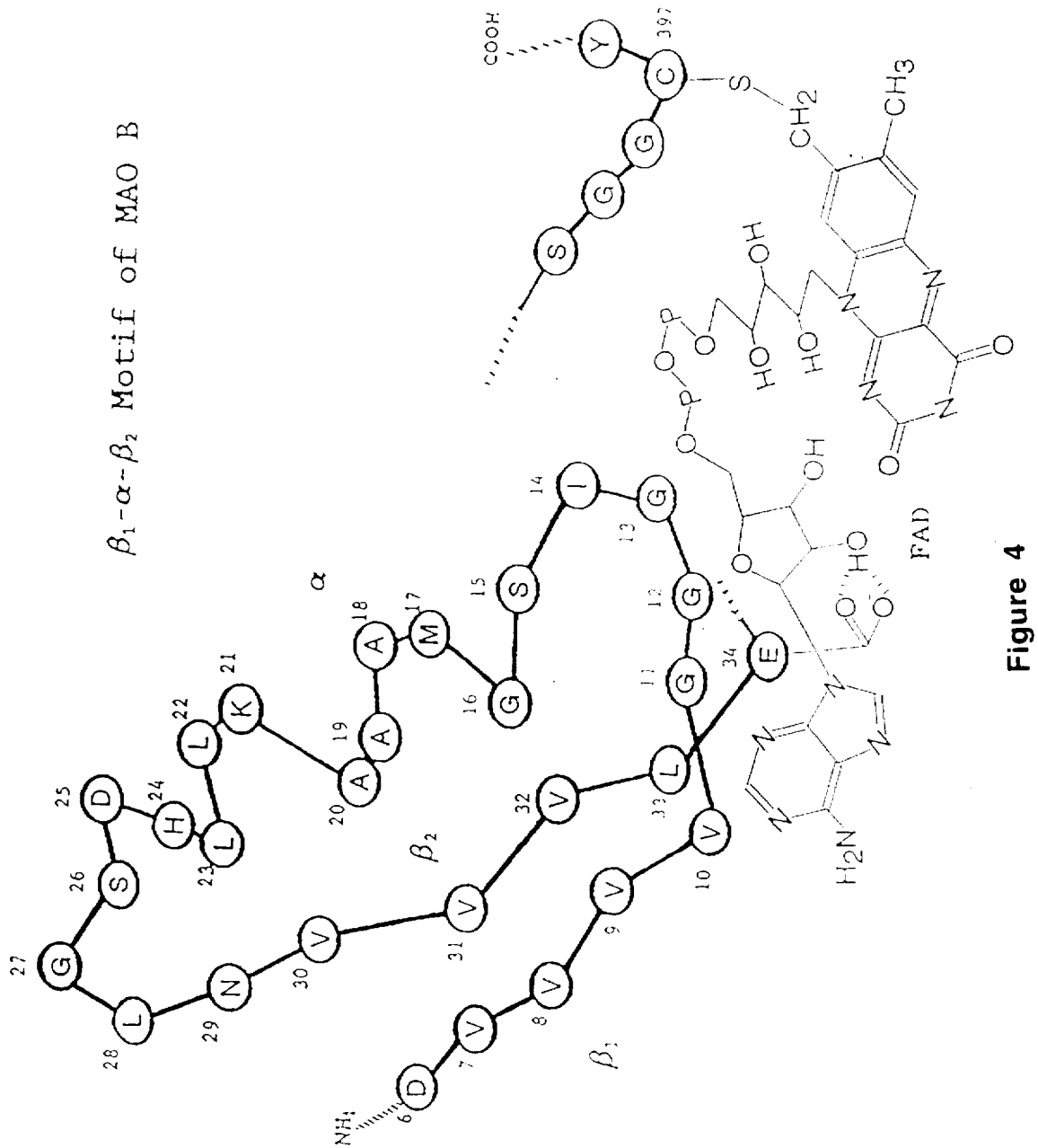
FIG. 4 shows a diagram of the putative dinucleotide-binding site DBS ($\beta_1$-$\alpha$-$\beta_2$ motif) and the covalent attachment site for FAD in human monoamine oxidase B. Thick and thin lines represent the peptide backbone and covalent bonds, respectively. Amino acids 6 through 34 comprise the dinucleotide-binding site in monoamine oxidase B. The initial residue, is usually a hydrophilic amino acid. In monoamine oxidase B, this residue is at position 6 and is aspartate. Glutamate at position 34, hydrogen bonds with the 2'-hydroxy group of ribose in the adenine monophosphate moiety of FAD. This position is almost always glutamate in proteins that contain the dinucleotide-binding site. The highly conserved glycines are important in allowing the FAD to approach glutamate-34. The dotted line to the right of glutamate-34 represents the continuing polypeptide chain which is next depicted to the right at serine-394. Cysteine-397 forms a covalent linkage with FAD through the 8-$\alpha$ methyl group of the isoalloxazine ring.

FIG. 4 shows the level of monoamine oxidase B synthesized for the wild-type at different culture times. The peak production of monoamine oxidase B was reached at 48 hours, followed by a rapid decline in synthesis thereafter. Thus, all determinations were carried out 48 hours after electroporation.

EXAMPLE 10

Activity of Wild-Type and Mutant monoamine oxidase B

Monoamine oxidase B expressed in COS-7 cells was partially purified, and the amount of monoamine oxidase B for each sample was equalized prior to radiometric activity assays. As shown in TABLE I, the activity in mutants E34D, E34Q, and E34A was very low or undetectable. Of the three mutations at residue 34, only E34D, which is a highly conserved mutation from glutamate to aspartate, maintains any detectable monoamine oxidase B activity. Mutant V10I, is a highly conserved mutation in a region of the $\beta_1$-$\alpha$-$\beta_2$ motif not thought to be critical for enzymatic activity. This mutant was constructed as a control to ensure that the mutagenesis process was capable of producing active mutants, and any loss of catalytic activity in other mutants could be attributed to the identification of a critical residue required for enzymatic activity. Although the V10I mutant maintained high activity, it was only ~65% of that found for wild-type monoamine oxidase B (TABLE I). Molecular activity measurements were obtained in duplicates for each of a series of three separate experiments.

TABLE I

Comparative activities of wild-type and mutant monoamine oxidase B in COS-7 cells

| Sample | Molecular Activity μmole/min/mg MAO B | Percent of Wild-type Activity |
| --- | --- | --- |
| Wild-type | 1.29 ± 0.22 | 100 |
| V10I | 0.81 ± 0.03 | 64.7 ± 4.8 |
| E34D | 0.09 ± 0.01 | 7.4 ± 1.0 |
| E34Q | ND | ND |
| E34A | ND | ND |

EXAMPLE 11

Western Blot Analysis

Figure 3:
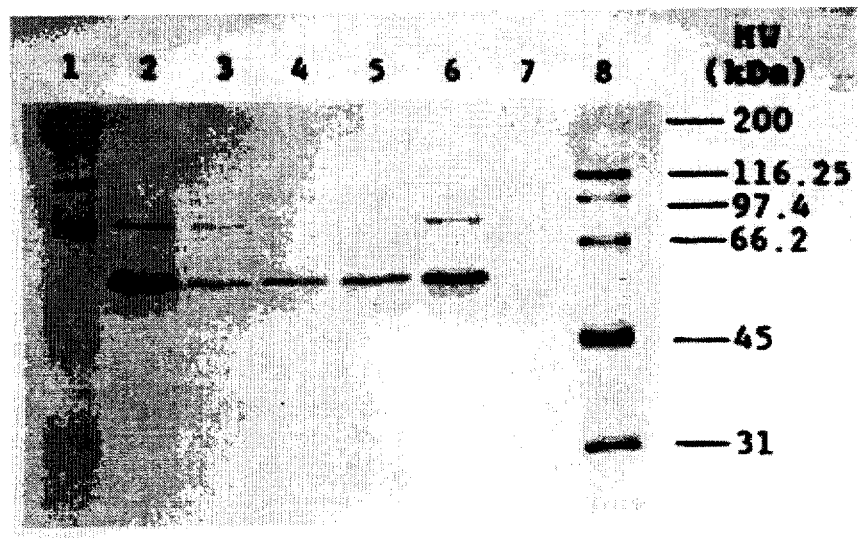
FIG. 3 shows a western blot of wild type and mutant monoamine oxidase B in transfected COS-7 cells. Expressed wild type and mutant monoamine oxidase B were immunoprecipitated using a polyclonal goat anti-monoamine oxidase B antibody and protein G beads as described below. The immunoprecipitated enzymes were separated on 10% sodium dodecyl sulfate-polyacrylamide gel electrophoresis (SDS-PAGE), transferred to a nitrocellulose membrane and analyzed by Western blotting using the monoamine oxidase B specific monoclonal antibody, monoamine oxidase B-1C2. Lane 1: prestained MW marker; Lane 2: wild type monoamine oxidase B; Lane 3: E34A monoamine oxidase B; Lane 4: E34Q monoamine oxidase B; Lane 5: E34D monoamine oxidase B; Lane 6: V10I monoamine oxidase B; Lane 7: untransfected COS-7 cells; Lane 8: biotinylated MW markers.

Monoamine oxidase B samples obtained from immunoprecipitation (above) were positively identified using the monoamine oxidase B-specific monoclonal antibody (monoamine oxidase B-1C2). As shown in FIG. 3, wild-type and monoamine oxidase B variants have a band corresponding to 59 kDa, whereas untransfected COS-7 cells show no detectable monoamine oxidase B. Wild-type, mutant, and untransfected COS-7 cells all have a faint band at a lower molecular weight (55 kDa) which is attributed to the heavy chain of the goat antibody. A faint band at about 80 kDa was consistently found but the origin of this is unknown.

EXAMPLE 12

The deduced amino acid sequences of human liver and placental monoamine oxidase A, bovine adrenal monoamine oxidase A, rat liver monoamine oxidase A, human liver monoamine oxidase B, human platelet and frontal cortex monoamine oxidase B and rat liver monoamine oxidase B have been determined. Approximately one-third of the sequence of bovine liver monoamine oxidase B has also been ascertained by direct amino acid sequencing. Comparison of these sequences shows monoamine oxidase A and B are strikingly similar in each respective enzyme among these three species. Two regions in human monoamine oxidase A (residues 15–43 and 389–460) and monoamine oxidase B (residues 6–34 and 380–451) contain a dinucleotide-binding site at the N-terminus that is found in the vast majority of flavin-requiring enzymes that bind FAD either non-covalently or covalently, and the FAD covalent binding site toward the C-terminus, respectively.

The present invention demonstrates that one amino acid ($Glu^{34}$) plays a crucial role in the dinucleotide binding site of monoamine oxidase B. Based on the crystal structures of glutathione reductase, p-hydroxybenzoate hydroxylase, lipoamide dehydrogenase and other proteins, this site is known to consist of a $\beta_1$-$\alpha$-$\beta_2$ motif that interacts with FAD, and it has a consensus sequence of Asp-Val-Val-Val-Ile-Gly-x-Gly-x-x-Gly-Leu-x-x-Ala-x-x-Leu-x-x-x-x-x-Val-x-Val-Leu-Glu. The polypeptide $Gly^{11}$-x-$Gly^{13}$-x-x-$Gly^{16}$, which constitutes a turn between the first P-sheet and the beginning of the $\alpha$-helix, is highly conserved in 28 flavoproteins. Also $Ala^{20}$ is highly conserved, and residues at positions 7–10, 12, 15, 17, 23, 30, 32, and 33 are usually hydrophobic. Furthermore, amino acids at position 6 are highly conserved hydrophilic residues, and the motif usually ends with glutamate residue 34. The γ-carboxylate group of glutamate is thought to bind to the 2'-hydroxy group of ribose of the AMP moiety of FAD to align this cofactor for participation in the oxidation-reduction cycle during catalysis of amines to their corresponding aldehydes. The putative structure of the $\beta_1$-$\alpha$-$\beta_2$ motif in monoamine oxidase B is shown in FIG. 4.

To illustrate the role of $Glu^{34}$ in dinucleotide binding, several mutant cDNAs to human monoamine oxidase B were constructed and transiently expressed in COS-7 cells. Various expression systems, which use different expression vectors, transfection methods, and cell lines produce varying amounts of monoamine oxidase B/mg total protein, which can contribute to different specific activity (units of monoamine oxidase B activity/mg total protein) values. Therefore, all activities were expressed in terms of molecular activity (units of monoamine oxidase B activity/mg monoamine oxidase B) which reflects the apparent catalytic activity of a known amount of expressed enzyme and permits activity measurements to be compared among wild-type and variant monoamine oxidase proteins. Molecular activity measurements in the expression system were found to be highly reproducible when activity assays were performed with a known amount of monoamine oxidase B protein. Thus, molecular activities of expressed monoamine oxidase B were determined after monoamine oxidase B protein was initially quantitated by ELISA so that all mutants and wild type monoamine oxidase B samples could be adjusted to equal concentrations before their activity was measured.

The molecular activity of wild type ($Glu^{34}$) was compared to E34D, E34Q, and E34A mutants. Variants E34Q and E34A were devoid of activity, and the activity of the E34D variant was reduced by 93% (TABLE I). The E34A mutant was inactive since the alanine substitution has little structural similarity to the glutamate residue and does not carry a negative charge. The negative charge is appears to be essential for interaction with the AMP moiety of FAD. The glutamine residue in E34Q is closest to the wild-type glutamate in size, but it also lacks a negative charge and resulted in complete loss of activity. However, for the mutant E34D, the dramatic decrease in activity was unexpected since a negative charge was retained. This could be due to the shorter side chain of the aspartate residue, which results in a loss of contact between its β-carboxylate group and the 2'-hydroxy group of the ribose in FAD. Assuming that the additional C—C bond length of glutamate is 1.54 Å and has a bond angle of 109.5°, the calculated distance between alternate carbons is about 2.52 Å. This translates to a decrease in length of the aspartate side chain by about 1.26 Å (half the distance of 2.52 Å), which would result in the loss of intermolecular bonding.

A fourth mutant (V10I) was also constructed to serve as a control. This variant protein contained $Ile^{10}$ in place of $Val^{10}$, which is positioned at the end of the first $β_1$-sheet before the $Gly^{11}$-x-$Gly^{13}$-x-x-$Gly^{16}$ turn. Analysis of this variant protein showed that it had approximately 65% of the wild type activity. Thus, the conservative substitutions in the non-critical residues of the $β_1$-α-$β_2$ motif have a much less pronounced effect on enzyme function. However, there was some reduction of enzymatic activity, which is probably a consequence of a slight conformational perturbation within the critical $β_1$-α-$β_2$ motif (FIG. 4). In contrast, replacement of $Glu^{34}$ with amino acid $Gln^{34}$, $Ala^{34}$, or $Asp^{34}$ resulted in a dramatic reduction of enzymatic activity.

The present invention represents the first illustration of the critical role of selected amino acids in the dinucleotide binding site for generating enzymatic activity. The present invention shows that $Glu^{34}$ is a crucial amino acid residue that participates in the function of monoamine oxidase B through non-covalent binding to the AMP moiety of FAD. FAD is covalently bound to $Cys^{397}$. Thus, FAD is positioned in the macromolecule by dual binding to residues $Glu^{34}$ and $Cys^{397}$. Because these two residues are located distally in the primary amino acid sequence of monoamine oxidase B, it is unknown whether FAD is first bound to the apoenzyme at the dinucleotide binding site and then delivered to $Cys^{397}$ or vice versa.

FAD functions as an electron acceptor in the oxidation of amines and is, therefore, likely to constitute part of or be adjacent to the catalytic site of monoamine oxidase. Furthermore, the dinucleotide binding site in the N-terminus of monoamine oxidase B and the site for covalent attachment of FAD towards the C-terminus of monoamine oxidase B are in close proximity through FAD linkage and consequently could form part of the active site for monoamine oxidase B. The substrate binding site(s) in monoamine oxidase remains unknown, but it may be in close proximity to $Glu^{34}$ or $Cys^{397}$.

In the present invention, site-directed mutagenesis was used to convert $Glu^{34}$ in monoamine oxidase B to Asp, Gln, and Ala. The wild-type and mutant cDNAs were then transiently transfected into COS-7 cells. All three variants exhibited a dramatic decrease in enzymatic activity as compared to wild-type monoamine oxidase B, and only the Asp variant retained any detectable activity. The present invention illustrates that the hydrogen bonding between the γ-carboxylate group of $Glu^{34}$ and the 2'-hydroxyl group of FAD is very critical for monoamine oxidase B enzymatic activity. Furthermore, FAD initially binds to the dinucleotidebinding site and then is delivered through folding of the macromolecule to the covalent binding site.

EXAMPLE 13

Design of MAO inhibitors

Based on the important role played by $Glu^{34}$, the present invention discloses novel FAD derivatives act as monoamine oxidase A and/or B inhibitors. One of these FAD derivatives is flavin deoxyadenine dinucleotide (dFAD), which lacks the critical 2'-hydroxyl group in the AMP moiety of FAD. A second FAD derivative of the present invention is flavin dideoxyadenine dinucleotide (ddFAD), which lacks both 2'- and 3'-hydroxyl group in the AMP moiety of FAD. The great advantage of the compounds of the present invention is that they mimic the native FAD structure but lack the critical 2'- and/or 3'-hydroxyl group. The present invention discloses that these FAD derivatives compete with FAD for monoamine oxidase B binding during the synthesis of monoamine oxidase in vivo. If these compounds are coupled into monoamine oxidase B during synthesis of the nascent polypeptide, the newly synthesized monoamine oxidase B would not acquire its catalytic activity due to the loss of a critical hydrogen bonding between the γ-carboxylate group of $Glu^{34}$ and the 2'-hydroxyl group of the AMP moiety of FAD. In other words, monoamine oxidase B enzymatic activity would be dramatically inhibited by these FAD analogs. The effects of the novel FAD analogs of the present invention are shown in a riboflavin-depleted (Rib⁻) COS-7 cell line. Since mammalian cells are not capable of synthesizing FAD, and these Rib⁻ COS-7 cells contain very low levels of endogenous flavin, newly synthesized proteins should contain very low levels of FAD By adding monoamine oxidase cDNA with these FAD analogs in Rib⁻ COS-7 cells via electroporation, one can observe that these FAD analogs restore monoamine oxidase enzymatic activity. Furthermore, the present inventions shows that these FAD analogs compete with FAD for binding to monoamine oxidase by introducing monoamine oxidase cDNAS and these compounds into Rib⁻ COS-7 cells with different concentrations of FAD.

EXAMPLE 14

Synthesis of dFAD and ddFAD

Synthesis of dFAD and ddFAD is carried out by a modified method of DeLuca et al., (1956) *J Biol. Chem.* 223, 569–576, which has been used to prepare synthetic FAD for many years. This method involves a direct chemical condensation to form a phosphate diester bond between riboflavin-5'-phosphate (pyridinium salt) and deoxy- (or dideoxy-) adenosine-5'-phosphoramidate under anaerobic conditions. Briefly, commercially available sodium riboflavin-5'-phosphate (Sigma) is mixed thoroughly with 2'-deoxyadenosine-5'-monophosphate in a dry round bottom flask and 50 ml of trifluoroacetic acid anhydride (TFAA) is added in small portions with continuous stirring. After all of the trifluoroacetic acid anhydride is added and the solids are completely dissolved, the round bottom flask containing the dark amber colored mixture is sealed and allowed to stand at room temperature in the dark for about 16 hours with gentle stirring. At the end of this period of time, the round bottom flask is connected in a vacuum and excess TFAA is removed until a black, thick and gummy residue remained. This residue is then titrated with 200 ml of cold anhydrous ether. The resulting bright yellow-orange precipitate is centrifuged, washed twice with additional 80 ml of cold anhydrous ether and then dried under vacuum. Cold absolute ethanol (100 ml), saturated with ammonia gas, is added to the dried yellow powder. The solid is thoroughly suspended and placed on ice for 30 minutes. The suspension is centrifuged and the precipitate again placed on ice for 10 minutes after resuspension in another 100 ml of ammonia saturated ethanol. The precipitate is centrifuged, washed twice with 80 ml of cold absolute alcohol and dried.

The yellow residue obtained from above is dissolved in distilled water. The solution is adjusted to pH 7.0 with dilute ammonia and carefully applied to a DEAE-cellulose column (chloride form). The column is first washed with water, and then elution is continued using 0.003N hydrochloric acid containing 0.015N lithium chloride, which removes 2'-deoxyadenosine-5'-monophosphate followed by riboflavin-5' monophosphate. Hydrochloric acid (0.003 N) containing 0.035N lithium chloride eluted 2'-deoxy FAD as a discrete band (ration of O.D. at 260 nm vs 450 nm is 3.26, pH 7.0). The 2'-deoxy-FAD fraction is adjusted to pH 6.0 with dilute lithium hydroxide and evaporated to a small volume. This concentrated yellow solution is again adjusted to pH 6.0 and loaded on a C-18 semi-preparative column. Elution is performed with a linear gradient from 95% A and 5% B (A=10 mM ammonium phosphate buffer, pH 6.8, B=acetonitrile) to 88% A and 12% B in 50 minutes with a flow rate of 4 ml/minute. 2'-deoxy-FAD is eluted as a discrete peak with a retention time of 26 minutes. This compound is collected in silicone coated glass slides, dried in a speedvac and stored at −20° C. as a yellow powder. The authenticitiy of 2'-deoxy-FAD was confirmed by mass spectrometry and NMR analysis.

EXAMPLE 15 dFAD or ddFAD as substituted cofactors and inhibitors of monoamine oxidase

The use of dFAD or ddFAD, synthesized as described above, as monoamine oxidase B co-factors and inhibitors in the Rib-COS-7 cell line. First, monoamine oxidase B cDNA and dFAD (or ddFAD) is introduced into Rib⁻ COS-7 cells by electroporation. Monoamine oxidase B cDNA is transfected into Rib⁺ and Rib⁻ COS-7 cells, which serve as positive and negative controls, respectively. Since dFAD and ddFAD cannot serve as substituted cofactors of monoamine oxidase B, monoamine oxidase B enzymatic activity will be low or absent when dFAD or ddFAD are added during the transfection process into Rib⁻ COS-7 cells with monoamine oxidase B cDNA. Second, monoamine oxidase B cDNA and dFAD or ddFAD is introduced into Rib⁻ COS-7 cells with the addition of different concentrations of exogenous FAD. dFAD or ddFAD competes with FAD for binding to monoamine oxidase B. The same work is performed with monoamine oxidase A cDNA.

Flavin 2'-deoxyadenosine dinucleotide (dFAD) was synthesized as described above. Synthetic dFAD was purified by resolution on HPLC to yield a major sharp peak on the chromatogram. The authenticitiy of dFAD was confirmed by mass spectrometry and NMR analysis.

EXAMPLE 16

Mutagenesis at a Highly Conserved Tyrosine in Monoamine Oxidase B Affects FAD Incorporation and Catalytic Activity The present invention shows that Glu-34 is required for catalytic activity, presumably by forming a hydrogen bond between the carboxylate group of glutamate and the 2'-hydroxyl group of ribose in the AMP moiety of FAD. A third FAD binding site in MAO B (residues 39–46) has been identified by sequence comparisons to other flavoenzymes. The conserved sequence contains a tyrosine residue (Tyr-44) which, based on the X-ray crystal structure of ferredoxin-NADP⁺ reductase, is postulated to participate in FAD binding through van der Waals contact with the isoalloxazine ring and a hydrogen bond to the 3'-hydroxy of the ribityl moiety. To show the role of this tyrosine residue, site-directed mutants that encode substitutions at Tyr-44 were prepared and expressed in mammalian COS-7 cells. Variant MAO B enzymes were then characterized with respect to enzymatic activity and [$^{14}$C] FAD incorporation. Substitution of tyrosine with phenylalanine had no effect on MAO B activity or the level of [$^{14}$C] FAD incorporation compared to the wild-type enzyme, indicating that the hydroxyl group of the tyrosine residue was not essential at residue 44. Substitution of tyrosine with serine or alanine, however, which do not have an aromatic ring, resulted in a dramatic decrease in enzymatic activity and FAD incorporation. Thus, the aromatic ring of the tyrosine residue at position 44 is required for FAD binding and catalytic activity of MAO B.

Sequence comparisons of MAO A and B to other flavoproteins indicate the presence of a third FAD binding site. In MAO B, this segment (residues 39–46) of high sequence identity is located in the N-terminal region of the enzyme in close proximity to the FAD dinucleotide-binding motif (residues 6–34). The homologous sequence occurs in NADPH-sulfite reductase, NADH nitrate reductase, NADPH-cytochrome P-450 oxidoreductase, ferredoxin-NADP⁺ reductase (FNR), and NADH-cytochrome b5 reductase and is thought to be involved in noncovalent FAD binding in these enzymes. The crystal structure of FNR has been determined, and the entire FAD binding domain was characterized. This domain was shown to consist of an antiparallel β-barrel not previously observed in other flavoproteins. A short sequence containing a tyrosine residue was shown to reside within a β-sheet in close proximity to FAD. The tyrosine residue is thought to make extensive van der Waals contact with the isoalloxazine moiety and to form a hydrogen bond with the 3'-hydroxy of the ribityl moiety of FAD. Since the similar sequence in MAO B is in close proximity to the known FAD dinucleotide binding region, it seems possible that the conserved tyrosine (Tyr-44) has a similar function in MAO B.

To illustrate that this tyrosine interacts with FAD in MAO B, mutants that encode substitutions at Tyr-44 were prepared and expressed in mammalian COS-7 cells. Substitutions (Tyr to Phe, Ser or Ala) were selected to permit analysis of the aromatic and hydrogen bonding roles of the tyrosine residue with FAD. The aromatic ring of the tyrosine residue is essential for FAD binding and catalytic activity in MAO B, but hydrogen bonding through the hydroxyl group is not critical. Based upon these findings, a model of how FAD interacts with three binding sites in MAO B was constructed, and the sequence of events that occur during the flavinylation process was examined.

EXAMPLE 17

Site-directed Mutagenesis

Mutagenesis was performed by the method of Deng and Nickoloff (1992) using a "Transformer Site-directed Mutagenesis" kit (Clontech) as described above. The mutagenic primers and the corresponding amino acid changes are shown in FIG. 5. Tyr at position 44 was replaced with Phe in Y44F, Ser in Y44S and Ala in Y44A. The Leu residue at position 46 was replaced with Val in L46V. All mutagenic primers were designed to create a new restriction site, without altering the coding sequence of any other amino acids, for the purpose of screening.

Construction of mutants Y44F and L46V was carried out in the pBluescript SK vector (Stratagene) with human MAO B cDNA inserted at the EcoRI site. A HpaI restriction site was introduced into a 30-mer selection primer to replace the only KpnI site in the plasmid vector. For initial screening of mutants, clones were picked from an NZCYM/ampicillin plate and inoculated into a microcentrifuge tube containing 0.5 ml NZCYM/ampicillin and incubated with shaking for 4 hours at 37° C. An aliquot (50 µl) of the mini-culture was stored at 4° C. for future propagation. The remaining 450 μl was spun down and processed by the alkaline lysis method in a total volume of 45 μl. The supernatant was ethanol precipitated and the DNA screened by restriction analysis for the presence of a new restriction site created by the mutagenic primer. The mutant cDNAs were then subcloned into the pSVK3 expression vector (LKB-Pharmacia) at the EcoRI site and screened for the sense orientation.

Construction of mutants Y44A and Y44S was carried out directly within the expression vector pSVK3 with human MAO B cDNA inserted into the EcoRI site. A HpaI restriction site was introduced into a 29-mer selection primer to replace the only KpnI site in the pSVK3 vector. The mutant clones were screened for the presence of the new restriction site created by the mutagenic primer as described above. The presence of the correct mutations in all mutant cDNAs were confirmed by double-stranded dideoxy DNA sequencing. Both wild-type and mutant plasmid DNAs were purified through CsCl-gradients prior to transfection studies.

EXAMPLE 18

Expression of Wild type or Mutant MAO B cDNAs.

Mammalian COS-7 cells used for MAO B expression were grown in Dulbecco's Modified Eagle Medium (DMEM) with 10% fetal bovine serum (FBS) and 5% $CO_2$ at 37° C. Riboflavin-depleted COS-7 cells were generated by maintaining these cells in riboflavin-free DMEM-FBS (Gibco) for greater than 100 days. Transient transfection by electroporation (Zimmerman et al., 1982) of wild-type or mutant MAO B cDNAs into COS-7 cells was carried out as described above. Briefly, cells were harvested during late log phase growth and resuspended in DMEM supplemented with 10% FBS. Wild-type or mutant cDNA (15 μg) was then electroporated into the cells ($2.5 \times 10^6$ cells/ 0.8 ml DMEM-FBS). In experiments where flavinylation of wild-type or variant MAO B was studied, 20 μl of 0.8 mM [$^{14}$C] FAD and 15 μg of MAO B cDNA were simultaneously electroporated into riboflavin-depleted COS-7 cells in riboflavin-free medium ($2.5 \times 10^6$ cells/0.8 ml). Transfected cells were resuspended in 15 ml of DMEM/FBS (or riboflavin-free DMEM-FBS) and incubated at 37° C. with 5% $CO_2$. Cells were harvested at 48 hours and homogenized in a lysis solution (500 μl) containing 20 mM Tris-HCl, 1.0 mM EDTA, and 0.5 mM PMSF (phenylmethylsulfonyl fluoride), pH 8.0. Extraction of MAO B from each sample was carried out by addition of Triton X-100 to a concentration of 0.25% and stirring for 30 minutes at RT.

EXAMPLE 19

Enzyme Linked Immunosorbance Assay (ELISA)

Protein concentrations of samples containing wild-type or variant MAO B were determined by a Micro-BCA kit (Pierce). All samples were then adjusted to equal protein concentration prior to quantitation of MAO B by ELISA using a modification of the method of Yeomanson and Billett (1992) as described above. Expression levels of wild-type or variant MAO B were determined in duplicate for three separate experiments.

EXAMPLE 20

Enzyme Activity Determination

MAO B activity was measured by a modification of the method of Wurtman and Axelrod (1963). This modification allows accurate activity measurements in small amounts of MAO B (as low as 5 ng) expressed in cultured cells. For quantitative comparisons of wild-type and variant MAO B, all samples were adjusted to equal protein concentration and 10 μl of cell lysate (containing wild-type or variant MAO B) was incubated in an assay mixture (200 μl) containing 0.05M sodium phosphate buffer, pH 7.4, 3.6 nmole of 55 mCi/mmole [$^{14}$C] benzylamine hydrochloride, and 10 nmoles of unlabeled benzylamine. For each experiment, controls were assayed concurrently, including cell lysate-free assay buffer, and nontransfected COS-7 cell lysate. After incubation at 37° C. for 9 minutes, all reactions were terminated with 6N HCl (25 μl) and placed on ice for 2 minutes. The reaction product was extracted with toluene (500 μl) and centrifuged at 10,000 xg for 5 minutes. The organic phase was counted in liquid scintillation fluid (Bio-Safe) in a Beckman LB3801 model liquid scintillation counter. The activites of wild-type and variant MAO B enzymes were determined in duplicate in three separate experiments.

EXAMPLE 21

Immunoprecipitation of Wild-type and Variant MAO B

Transfected COS-7 cells were homogenized in 300 μl of 20 mM Tris HCl, 1 mM EDTA, 0.5 mM PMSF, pH 8.0 and MAO B was extracted with 0.25% Triton X-100 for 30 minutes at 4° C. After centrifugation at 1300 xg for 5 minutes, an aliqout of each supernatant was assayed by ELISA and all supernatants were adjusted to equal MAO B concentrations. The supernatants (300 μl) were then incubated with 10 μg of goat polyclonal anti-MAO B antibody overnight at 4° C. Protein-G Sepharose beads were added (50 μl) and the samples were further incubated for 3 hours. The protein-G sepharose/goat antibody/MAO B immunocomplex was collected by centrifugation at 10,000 xg for 20 seconds, and washed 6 times with 20 mM Tris buffer, pH 8.0. The immunocomplex was eluted with SDS-PAGE sample buffer and subsequently analyzed by Western blot or fluorography.

EXAMPLE 22

Western Blot Analysis and Fluorography

The immunoprecipitated proteins (obtained as described above) were subjected to electrophoresis in a 10% SDS-polyacrylamide gel and analyzed by Western blotting as described above. Immunoprecipitated wild-type and variant MAO B were subjected to electrophoresis in a 10% SDS-polyacrylamide gel. The gel was fixed in 7% acetic acid, 10% methanol and 83% $H_2O$ for 1 hour and processed for fluorography as described by Bonner and Laskey (1974). The dried gel was exposed to Kodak X-OMAT AR film at −80° C.

All expression studies were carried out in mammalian COS-7 cells, since they do not contain any detectable endogenous MAO B, as determined by ELISA, Western blot and radiometric activity assays. Expression parameters were optimized for wild-type MAO B prior to studying variant MAO B or apo-MAO B. Optimal transient expression was achieved by electroporating 15 μg of cDNA into COS-7 cells at log phase growth ($2.5 \times 10^6$ cells/800 μl DMEM-FBS). Maximum expression of MAO B was obtained 48 hours after transfection, yielding approximately 1.0 μg MAO B/mg cellular protein.

Expression levels of wild-type and variant MAO B enzymes are shown in TABLE II. The amount of MAO B expressed for all variants shows no significant difference from that of wild-type MAO B ($897 \pm 17$ ng MAO B/mg protein). The average protein concentration in the 500 μl cell lysates was $2.23 \pm 0.24$ mg/ml. Thus, each expression resulted in a yield of approximately 1 μg of MAO B.

TABLE II

Comparison of expression levels and activity in wildtype and variant MAO B[a]

| Enzyme | [MAO B] (ng MAO B/ mg protein) | Specific Activity (nmol/min/mg prot.) | Enzymatic Activity (μmol/ min/mg/MAO B) |
|---|---|---|---|
| WT | 897 ± 17 (100)[b] | 1.01 ± 0.07 (100)[b] | 1.13 ± 0.08 (100)[b] |
| Y44F | 873 ± 56 (97) | 0.92 ± 0.08 (91) | 1.05 ± 0.04 (93) |
| Y44S | 891 ± 36 (99) | 0.02 ± 0.003 (2) | 0.02 ± 0.003 (2) |
| Y44A | 864 ± 19 (96) | 0.01 ± 0.007 (1) | 0.01 ± 0.008 (1) |
| L46V | 896 ± 26 (100) | 0.84 ± 0.07 (83) | 0.94 ± 0.090 (83) |

[a]Samples were run in duplicate in each experiment. Each value represen the mean ± SE from three experiments. [b]Percent of wild type values are show in parenthesis.

Figure 6:
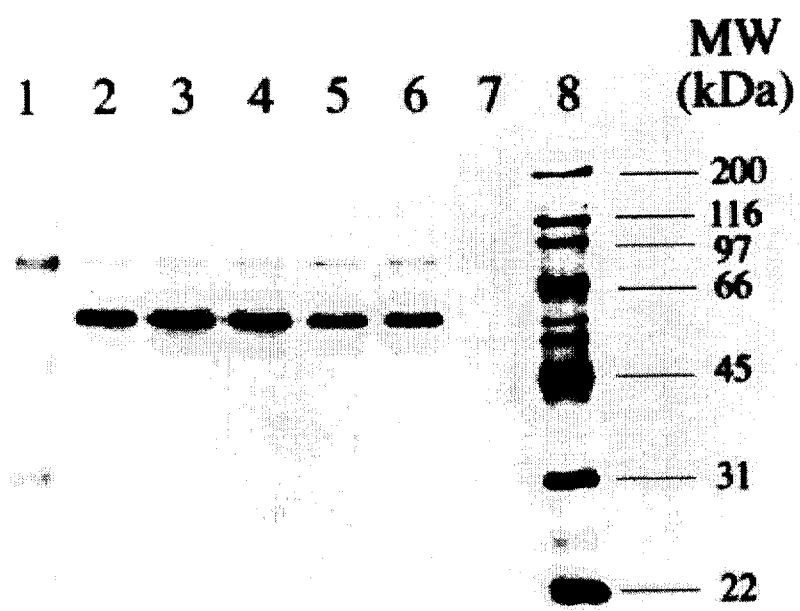
FIG. 6 shows a western blot analysis of wild-type and mutant MAO B cDNAs were transfected in COS-7 cells. Expressed wild-type and variant MAO B enzymes were adjusted to equal concentrations based on ELISA results before immunoprecipitation. The immunoprecipitated enzymes were separated on 10% SDS-PAGE, transferred to a nitrocellulose membrane and analyzed by Western blotting using the MAO B specific monoclonal antibody, MAO B-1C2. Lane 1: Prestained MW marker; Lane 2: wild-type MAO B; Lane 3: Y44F MAO B; Lane 4: L46V MAO B; Lane 5: Y44A MAO B; Lane 6: Y44S MAO B; Lane 7: untransfected COS-7 cells; Lane 8: Biotinylated MW marker.

Expressed MAO B was further identified by Western blotting. Wild-type and variant MAO B were adjusted to equal concentrations based on ELISA results, and immunoprecipitated with goat anti-MAO B polyclonal antibodies. The immunoprecipitated wild-type and variant MAO B enzymes were positively identified using a monoclonal antibody specific to MAO B (MAO B-1C2). As shown in FIG. 6, wild-type and variant MAO Bs have a band of equal intensity corresponding to 59 kDa, whereas the untransfected COS-7 cells show no MAO B band.

The activity of expressed wild-type and variant MAO B was determined in duplicate for three separate experiments by a radiometric assay using benzylamine as substrate. Substitution of Tyr-44 with phenylalanine in Y44F resulted in only a slight decrease (93% of wild-type) in enzymatic activity (Table II). However, substitutions of tyrosine to serine and alanine in Y44S and Y44A, respectively, resulted in a dramatic loss of MAO B activity. A fourth mutant, L46V, was constructed to serve as a control. This mutant cDNA encodes a variant protein containing Val-46 in place of Leu-46 at a site near the critical tyrosine residue. Because Val-46 was not highly conserved among the other flavoenzymes and has not been postulated to play a role in FAD binding, a mutation at this site was not expected to have a dramatic effect on MAO B activity. In fact, the L46V variant showed only a slight loss of enzymatic activity (83% of wild-type). Furthermore, the enzymatic activities (umol/min/mg MAO B) of all the variants closely correlated with their specific activities (μmol/min/mg protein). MAO B variants retaining the aromatic moiety at position 44 retained enzymatic activity, whereas those without the aromatic moiety (Y44S and Y44A) were nearly devoid of enzymatic activity.

To show the flavinylation of wild-type and variant MAO B enzymes, riboflavin-depleted COS-7 cells were produced by maintaining cells in riboflavin-free medium for greater than 100 days. Wild-type MAO B cDNA was transfected into these cells at 1 week intervals during the process of riboflavin depletion to monitor the effect on MAO B expression and activity. Expression levels of MAO B remained constant (approximately 1 μg/mg protein) throughout the process of riboflavin depletion. MAO B activity in sequential transfections, however, decreased rapidly as the endogenous riboflavin was depleted from the COS-7 cells. After 100 days of riboflavin depletion, transiently expressed apo-MAO B was completely devoid of activity. Cells grown continuously in riboflavin-free medium for greater than five months showed no detectable change in morphology. Furthermore, trypan blue staining did not detect the presence of damaged cells.

Figure 7:
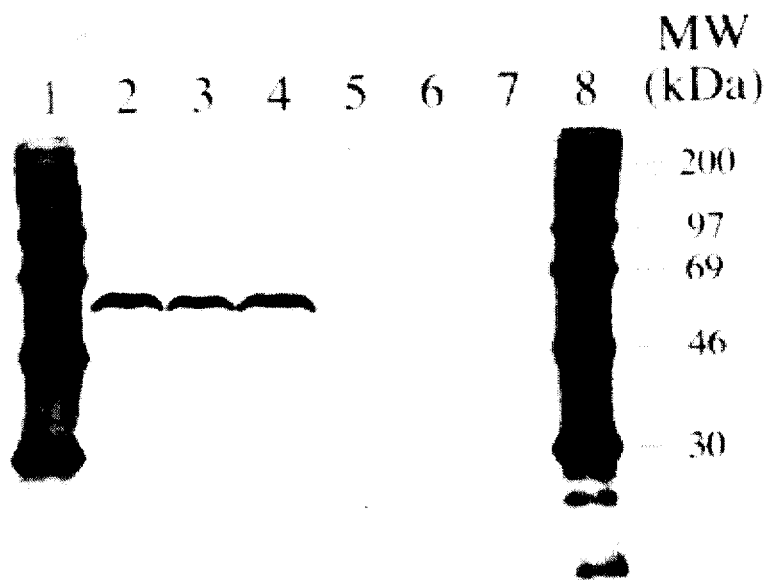
FIG. 7 shows a fluorogram of wild-type and mutant cDNAs were transfected in riboflavin-depleted COS-7 cells with the addition of exogenous [$^{14}$C] FAD during electroporation. Expressed wild-type and variant MAO B enzymes were adjusted to equal concentrations based on ELISA before immunoprecipitation. The immunoprecipitated enzymes were separated on 10% SDS-PAGE and analyzed by fluorography. Lane 1: [1 $^4$C] methylated MW marker; Lane 2: wild-type MAO B; Lane 3: Y44F MAO B; Lane 4: L46V MAO B; Lane 5: Y44A MAO B; Lane 6: Y44S MAO B; Lane 7: untransfected riboflavin-depleted COS-7 cells; Lane 8: [$^{14}$C] methylated MW marker.

Riboflavin-depleted COS-7 cells cannot synthesize FAD. Consequently, expressed MAO B is devoid of an FAD cofactor. Flavinylation of wild-type and variant MAO B enzymes was studied in these cells by simultaneous electroporation of [$^{14}$C] FAD with MAO B cDNA. The expressed enzymes were first adjusted to equal MAO B concentrations based on ELISA, followed by immunoprecipitation using goat anti-MAO B polyclonal antibodies. The immunoprecipitated MAO B was then subjected to SDS-PAGE and analyzed by fluorography. The amount of [$^{14}$C] FAD incorporated into wild-type or variant MAO B was determined by the intensity of banding on the fluorogram. As seen in FIG. 7, the wild-type and variants L46V and Y44F were capable of incorporating [$^{14}$C] FAD, as observed by dark bands of equal intensity at a molecular weight of about 59 kDa. However, Y44S and Y44A, which do not contain an aromatic moiety at position 44, showed only very faint bands.

The role of one amino acid (Tyr-44) in MAO B which is highly conserved among several flavoenzymes was shown. To illustrate the role of Tyr-44 in MAO B, the tyrosine residue was replaced with phenylalanine (Y44F), serine (Y44S), or alanine (Y44A). Interestingly, substitution of tyrosine with phenylalanine (Y44F), which does not have a hydroxyl group, resulted in only a 7% decrease in enzymatic activity as compared to the wild-type. If the hydroxyl group of Tyr-44 forms a hydrogen bond to the ribityl 3'-hydroxy of FAD, as in FNR to align FAD for catalysis, one would expect a significant decrease in enzymatic activity in variants that cannot participate in hydrogen bonding at position 44. Since little activity was lost with the Y44F variant, the hydroxyl group of Tyr-44 is not critical for MAO B activity. To assess the role of the aromatic ring in Tyr-44, this amino acid was also replaced with either serine or alanine, both of which do not have the aromatic group. These two variants showed a dramatic loss in activity, retaining only 2% and 1% of wild-type enzymatic activity, respectively. Thus, the aromatic ring of Tyr-44 is essential for MAO B catalytic activity.

The expression of wild-type and variant MAO B enzymes were evaluated by ELISA using polyclonal anti-MAO B antibodies. Since quantitation is dependent upon recognition by polyclonal antibodies at multiple epitopes under nondenaturing conditions, major conformational changes could affect quantitation. Furthermore, major conformational changes could result in the formation of insoluble inclusion bodies. The expression assays described herein show that the concentration of all MAO B variants was within 4% of the wild-type level, indicating that activity losses in the mutants were not due to anomalies in expression or conformational changes in the proteins.

In studies on flavinylation of these enzymes, wild-type MAO B was found to incorporate [$^{14}$C] FAD, observed as a single dark band on the fluorogram (FIG. 7). Also, Y44F, which retains the aromatic ring at position 44, incorporated covalently bound [$^{14}$C] FAD, as seen by a band of equal intensity to the wild-type. However, Y44S and Y44A, which lack the aromatic ring, showed only very faint bands, indicating that very little [$^{14}$C] FAD was incorporated. Thus, the loss of activity observed for these two variants can be attributed to their inability to bind FAD. Thus, an aromatic residue is required at position 44 for flavinylation to occur.

The inability of MAO B variants that do not contain an aromatic residue at position 44 to incorporate FAD reveals important information about the process of flavinylation. If FAD first forms a covalent link to the apo-MAO B at Cys-397 and then binds to Tyr-44, one would expect all variants at position 44 to contain covalently bound FAD. Since variants Y44S and Y44A did not contain a significant amount of covalently bound FAD. FAD binds initially to Tyr-44 instead of Cys-397. Thus, the N-terminal region including Tyr-44 and Glu-34 forms topological prerequisites which are necessary for initial FAD binding. Once bound, the FAD cofactor is subsequently delivered to Cys-397 to form a stable thioether linkage. The aromatic ring of Tyr-44 plays a crucial role in binding to the aromatic isoalloxazine ring of FAD during the initial steps of flavinylation.

Figure 8:
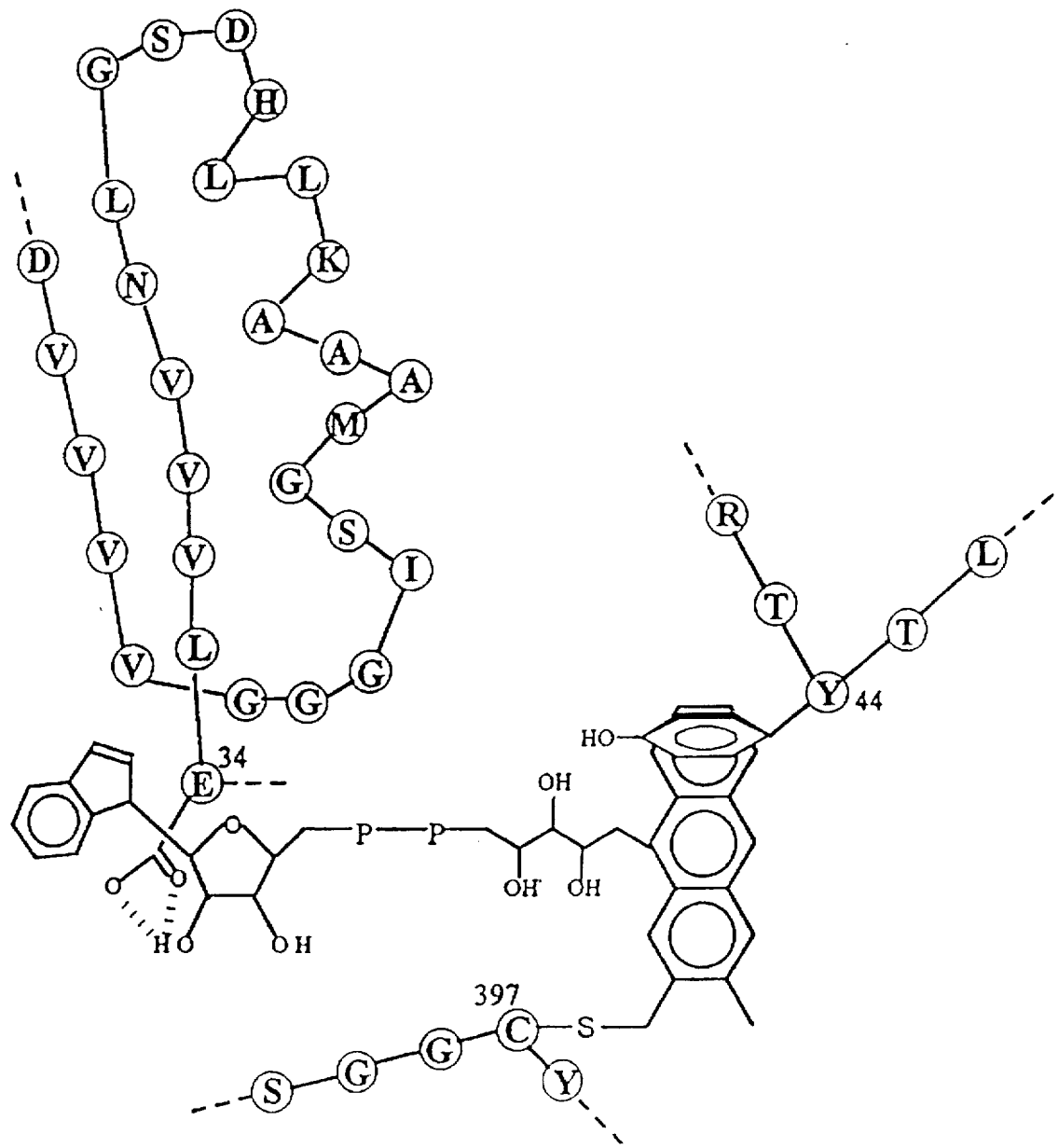
FIG. 8 shows a model of FAD interacting with three distinct binding sites of MAO B. Amino acids 6-34 comprise the dinucleotide-binding motif in MAO B. The glutamine residue of MAO B at position 34 forms a hydrogen bond with the 2'-hydroxy group of ribose in the AMP moiety of FAD. Cys-397 forms a covalent linkage with the flavin through the 8-$\alpha$-methyl group of FAD. A third FAD binding site is shown in which the aromatic moiety of Tyr-44 forms an essential contact with the isoalloxazine moiety of FAD. Variants that lack an aromatic ring at residue 44 show a dramatic decrease in their ability to incorporate FAD and in catalytic activity.

Binding of Tyr-44 to the isoalloxazine ring requires an aromatic-aromatic interaction. The analogous tyrosine in FNR appears on the si-face of the isoalloxazine ring tilted at an angle of approximately 53°. Such a geometric arrangement allows the hydrogen atoms on the edge of the aromatic ring to approach the p-electron cloud of the isoalloxazine ring. Burley and Petsko (1988) found that such edge-to-face interactions are approximately −1.5 Kcal/mol of stabilization energy, which is enthalpically favored over face-to-face aromatic stacking. Furthermore, they demonstrated that an interplanar angle of 55° is an enthalpically optimal geometric arrangement. While the bond angles of Tyr-44 in MAO B remain unknown without resolution of the three dimensional structure, the conservation of sequence and function within this short segment of amino acids may indicate a similar alignment. FAD is positioned in MAO B through noncovalent binding at Glu-34 and Tyr-44 and covalent linkage at Cys-397 (FIG. 8). Since FAD forms part of the active site in MAO B by functioning as an electron acceptor in the oxidation of amines, it is likely that these three FAD binding sites together form part of the catalytic pocket in MAO B.

Any patents or publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A modified synthetic flavin adenine dinucleotide compound which interacts with glutamate-34 of monoamine oxidase said flavin adenine dinucleotide compound modified by removing a hydroxyl group from the adenosine monophosphate moiety.

2. A pharmaceutical composition, comprising the compound of claim 1 and a pharmaceutically acceptable carrier.

3. A method of inhibiting monoamine oxidase ezymatic activity in a cell, comprising the step of contacting said cell with a pharmacologically effective dose of a modified synthetic flavin adenine dinucleotide compound which interacts with glutamate-34 of monoamine oxidase, said flavin adenine dinucleotide compound is modified by removing a 3'-hydroxyl group from the adenosine monophosphate moiety.

* * * * *

UNITED STATES PATENT AND TRADEMARK OFFICE
CERTIFICATE OF CORRECTION

PATENT NO. : 5,756,479
DATED : May 26, 1998
INVENTOR(S) : Abell et al.

It is certified that error appears in the above-identified patent and that said Letters Patent is hereby corrected as shown below:

Column 3,
Line 39, "wild type" should read --wildtype--.
Line 47, "wild type" should read --wildtype--.
Line 59, please remove the comma after the word "residue".

Column 4,
Line 34, "1$^4$C" should read --$^{14}$C--.

Column 6,
Line 36, "subdloned" should read --subcloned--.

Column 7,
Line 2, "xg" should read --x g--.
Line 6, "x g" should read --x g--.

Column 10,
Line 64, please remove the word "is" between the words "charge" and "appears".

Column 11,
Line 67, please insert the word "that" between the words "discloses" and "novel".

Column 15,
Line 6, "subdloned" should read --subcloned--.

UNITED STATES PATENT AND TRADEMARK OFFICE
CERTIFICATE OF CORRECTION

PATENT NO.   : 5,756,479
DATED        : May 26, 1998
INVENTOR(S)  : Abell et al.

It is certified that error appears in the above-identified patent and that said Letters Patent is hereby corrected as shown below:

Column 17,
Line 15, "show" should read --shown--.

Column 18,
Line 39, please remove the word "were" and replace it with "was".

Column 31,
Line 13, the number "43" should read --34--.
Line 37, please insert a comma between the words "oxidase" and "said".
Line 43, please insert the words "in vitro," between the words "cell" and "comprising".

Signed and Sealed this

Thirty-first Day of July, 2001

*Nicholas P. Godici*

Attest:

Attesting Officer

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 30
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

```
CGAGGGGGGG    CCCGGGTACC    CAATTCGCCC                                    30
```

( 2 ) INFORMATION FOR SEQ ID NO:2:

( i ) SEQUENCE CHARACTERISTICS:
        ( A ) LENGTH: 30
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:2:

```
CGAGGGGGGG    CCCGGTTAAC    CAATTCGCCC                                        30
```

( 2 ) INFORMATION FOR SEQ ID NO:3:

( i ) SEQUENCE CHARACTERISTICS:
        ( A ) LENGTH: 32
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:3:

```
AATGTGTTGT    TCTGGAAGCC    CGGGACCGTG    TG                                  32
```

( 2 ) INFORMATION FOR SEQ ID NO:4:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:4:

```
AATGTGGTTG    TTCTGGACGC    CCGGGACCGT    GTG                                 33
```

( 2 ) INFORMATION FOR SEQ ID NO:5:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i i ) MOLECULE TYPE:

(A) DESCRIPTION: other nucleic acid (iii) HYPOTHETICAL: No (iv) ANTI-SENSE: No (vi) ORIGINAL SOURCE:
 (B) STRAIN:
 (C) INDIVIDUAL ISOLATE:
 (D) DEVELOPMENTAL STAGE:
 (F) TISSUE TYPE:
 (G) CELL TYPE:
 (H) CELL LINE:

(xi) SEQUENCE DESCRIPTION: SEQ ID NO:5:

AATGTGGTTG TTCTGCAGGC CCGGGACCGT GTG     33

(2) INFORMATION FOR SEQ ID NO:6:

(i) SEQUENCE CHARACTERISTICS:
 (A) LENGTH: 33
 (B) TYPE: nucleic acid
 (C) STRANDEDNESS: double
 (D) TOPOLOGY: linear (ii) MOLECULE TYPE:
 (A) DESCRIPTION: other nucleic acid (iii) HYPOTHETICAL: No (iv) ANTI-SENSE: No (vi) ORIGINAL SOURCE:
 (B) STRAIN:
 (C) INDIVIDUAL ISOLATE:
 (D) DEVELOPMENTAL STAGE:
 (F) TISSUE TYPE:
 (G) CELL TYPE:
 (H) CELL LINE:

(xi) SEQUENCE DESCRIPTION: SEQ ID NO:6:

AATGTGGTTG TTCTGGCGGC CCGGGACCGT GTG     33

(2) INFORMATION FOR SEQ ID NO:7:

(i) SEQUENCE CHARACTERISTICS:
 (A) LENGTH: 28
 (B) TYPE: nucleic acid
 (C) STRANDEDNESS: double
 (D) TOPOLOGY: linear (ii) MOLECULE TYPE:
 (A) DESCRIPTION: other nucleic acid (iii) HYPOTHETICAL: No (iv) ANTI-SENSE: No (vi) ORIGINAL SOURCE:
 (B) STRAIN:
 (C) INDIVIDUAL ISOLATE:
 (D) DEVELOPMENTAL STAGE:
 (F) TISSUE TYPE:
 (G) CELL TYPE:
 (H) CELL LINE:

(xi) SEQUENCE DESCRIPTION: SEQ ID NO:7:

CGACGTGGTC GTGGTGGGGG GCGGCATC     28

(2) INFORMATION FOR SEQ ID NO:8:

(i) SEQUENCE CHARACTERISTICS:
 (A) LENGTH: 28
 (B) TYPE: nucleic acid (C) STRANDEDNESS: double
                    (D) TOPOLOGY: linear (i i) MOLECULE TYPE:
                    (A) DESCRIPTION: other nucleic acid (i i i) HYPOTHETICAL: No (i v) ANTI-SENSE: No (v i) ORIGINAL SOURCE:
                    (B) STRAIN:
                    (C) INDIVIDUAL ISOLATE:
                    (D) DEVELOPMENTAL STAGE:
                    (F) TISSUE TYPE:
                    (G) CELL TYPE:
                    (H) CELL LINE:

(x i) SEQUENCE DESCRIPTION: SEQ ID NO:8:

CGACGTGGTC GTGATCGGGG GCGGCATC                                                                  28

(2) INFORMATION FOR SEQ ID NO:9:

(i) SEQUENCE CHARACTERISTICS:
                    (A) LENGTH: 6
                    (B) TYPE: amino acid
                    (C) STRANDEDNESS:
                    (D) TOPOLOGY: linear (i i) MOLECULE TYPE:
                    (A) DESCRIPTION: protein (i i i) HYPOTHETICAL: No (i v) ANTI-SENSE: No (v i) ORIGINAL SOURCE:
                    (B) STRAIN:
                    (C) INDIVIDUAL ISOLATE:
                    (D) DEVELOPMENTAL STAGE:
                    (F) TISSUE TYPE:
                    (G) CELL TYPE:
                    (H) CELL LINE:

(x i) SEQUENCE DESCRIPTION: SEQ ID NO:9:

Asp Val Val Val Ile Gly
                5

(2) INFORMATION FOR SEQ ID NO:10:

(i) SEQUENCE CHARACTERISTICS:
                    (A) LENGTH: 11
                    (B) TYPE: amino acid
                    (C) STRANDEDNESS:
                    (D) TOPOLOGY: linear (i i) MOLECULE TYPE:
                    (A) DESCRIPTION: protein (i i i) HYPOTHETICAL: No (i v) ANTI-SENSE: No (v i) ORIGINAL SOURCE:
                    (B) STRAIN:
                    (C) INDIVIDUAL ISOLATE:
                    (D) DEVELOPMENTAL STAGE:
                    (F) TISSUE TYPE:
                    (G) CELL TYPE:
                    (H) CELL LINE:

(x i) SEQUENCE DESCRIPTION: SEQ ID NO:10:

Asp Val Val Val Leu Glu Ala Arg Asp Arg Val
                5                   10

( 2 ) INFORMATION FOR SEQ ID NO:11:

( i ) SEQUENCE CHARACTERISTICS:
    ( A ) LENGTH: 9
    ( B ) TYPE: amino acid
    ( C ) STRANDEDNESS:
    ( D ) TOPOLOGY: linear ( i i ) MOLECULE TYPE:
    ( A ) DESCRIPTION: protein ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:11:

Asp Val Val Val Val Gly Gly Gly Ile
       5

( 2 ) INFORMATION FOR SEQ ID NO:12:

( i ) SEQUENCE CHARACTERISTICS:
    ( A ) LENGTH: 34
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:12:

CGTGTGGGAG GCAGGACTTA CACTCTTAGG AACC    34

( 2 ) INFORMATION FOR SEQ ID NO:13:

( i ) SEQUENCE CHARACTERISTICS:
    ( A ) LENGTH: 34
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:13:

CGTGTGGGAG GCAGAACGTT CACTCTTAGG AACC 34

( 2 ) INFORMATION FOR SEQ ID NO:14:

( i ) SEQUENCE CHARACTERISTICS:
        ( A ) LENGTH: 28
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:14:

GGGAGGCAGG ACGTCCACTC TTAGGAAC 28

( 2 ) INFORMATION FOR SEQ ID NO:15:

( i ) SEQUENCE CHARACTERISTICS:
        ( A ) LENGTH: 29
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:15:

GGGAGGCAGG ACGGCCACTC TTAGGAACC 29

( 2 ) INFORMATION FOR SEQ ID NO:16:

( i ) SEQUENCE CHARACTERISTICS:
        ( A ) LENGTH: 43
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:

```
         ( D ) DEVELOPMENTAL STAGE:
         ( F ) TISSUE TYPE:
         ( G ) CELL TYPE:
         ( H ) CELL LINE:

( x i ) SEQUENCE DESCRIPTION: SEQ ID NO:16:

GGCAGGACTT  ACACTCTTAG  GAACCAAAAG  GTTAAATATG  TGG                    4 3

( 2 ) INFORMATION FOR SEQ ID NO:17:

( i ) SEQUENCE CHARACTERISTICS:
              ( A ) LENGTH: 43
              ( B ) TYPE: nucleic acid
              ( C ) STRANDEDNESS: double
              ( D ) TOPOLOGY: linear ( i i ) MOLECULE TYPE:
              ( A ) DESCRIPTION: other nucleic acid ( i i i ) HYPOTHETICAL: No ( i v ) ANTI-SENSE: No ( v i ) ORIGINAL SOURCE:
              ( B ) STRAIN:
              ( C ) INDIVIDUAL ISOLATE:
              ( D ) DEVELOPMENTAL STAGE:
              ( F ) TISSUE TYPE:
              ( G ) CELL TYPE:
              ( H ) CELL LINE:

( x i ) SEQUENCE DESCRIPTION: SEQ ID NO:17:

GGCAGGACTT  ACACTGTTCG  AAACCAAAAG  GTTAAATATG  TGG                    4 3
```